United States Patent [19]

Sashin et al.

[11] 4,179,100
[45] Dec. 18, 1979

[54] RADIOGRAPHY APPARATUS

[75] Inventors: Donald Sashin; Ernest J. Sternglass, both of Pittsburgh, Pa.

[73] Assignee: University of Pittsburgh, Pittsburgh, Pa.

[21] Appl. No.: 820,424

[22] Filed: Aug. 1, 1977

[51] Int. Cl.² ............................................. G03B 41/16
[52] U.S. Cl. .............................. 250/416 TV; 250/366; 250/445 T
[58] Field of Search ................ 250/416 TV, 366, 401, 250/402, 445 T; 358/111

[56] References Cited

U.S. PATENT DOCUMENTS

| | | | |
|---|---|---|---|
| 3,833,810 | 5/1958 | Efanov | 250/273 |
| 3,837,657 | 6/1958 | Craig | 250/416 TV |
| 3,860,821 | 1/1975 | Barrett | 250/416 TV |
| 3,881,110 | 4/1975 | Hounsfield | 250/445 T |
| 3,927,318 | 12/1975 | Macovski | 250/272 |
| 4,031,395 | 6/1977 | Le May | 250/445 T |
| 4,045,672 | 8/1977 | Watanabe | 250/445 T |
| 4,051,379 | 9/1977 | Zacher | 250/445 T |

OTHER PUBLICATIONS

"Self Scanning Photodiode Arrays for Spectroscopy", Snow, Research-Development, Apr. 1976, pp. 18-22.

*Primary Examiner*—Craig E. Church
*Attorney, Agent, or Firm*—Arnold B. Silverman

[57] ABSTRACT

Radiography apparatus including radiation generating means, collimator means interposed between the radiation generating means and an object to be exposed to radiation, scintillator means disposed on the opposite side of the object from the radiation generating means for converting the radiation to light, a self-scanning, integrated array of photodiodes for receiving light and emitting responsive electrical signals, optical coupling means connecting the scintillator means to the self-scanning, integrated photodiode array and signal receiving means for storing, processing or displaying the electrical signals. Additional collimators may be employed if desired.

In a nuclear isotope embodiment, collimator means are provided between the object and the scintillator means.

The self-scanning array of photodiodes has one or more integrated circuit elements, each having a plurality of photodiodes, a storage capacitor on which to integrate electric charges and a multiplex switch for periodic readout by means of an integrated shift register scanning circuit.

36 Claims, 31 Drawing Figures

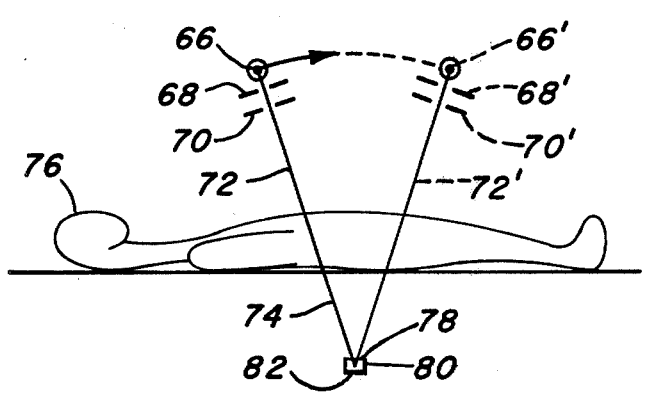
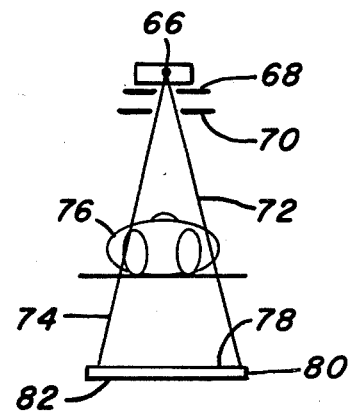
FIG. 3(a).  FIG. 3(b).
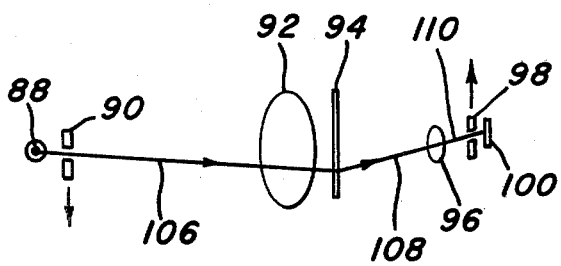
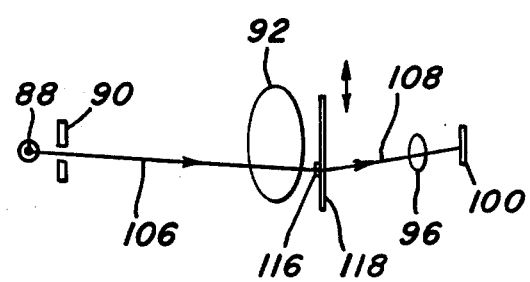
FIG. 4.  FIG. 5.
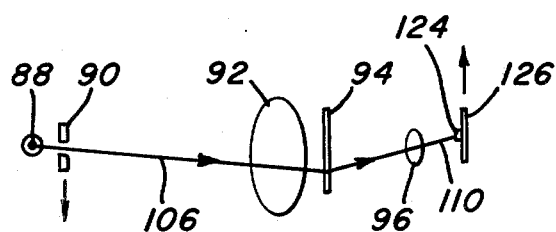
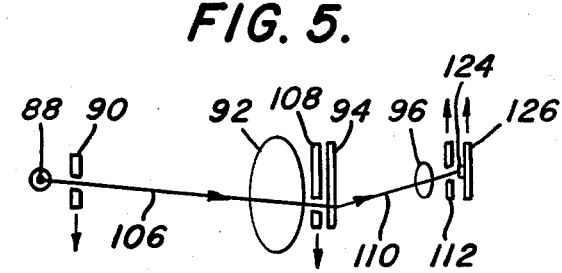
FIG. 6(a).  FIG. 6(b).
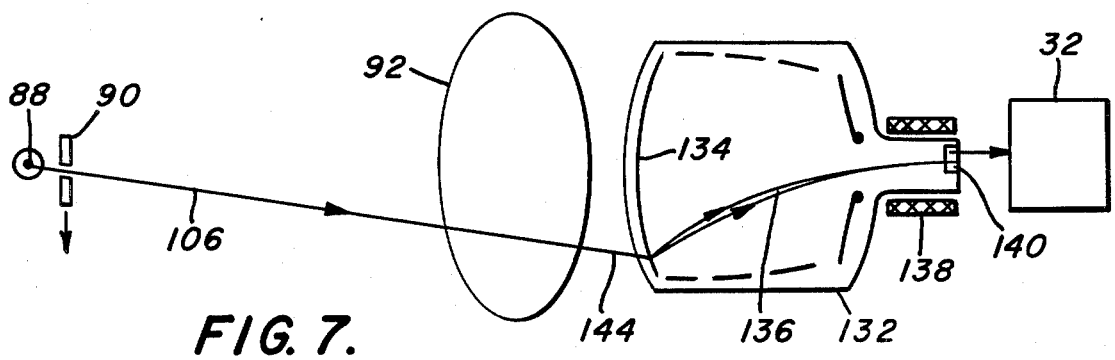
FIG. 7.

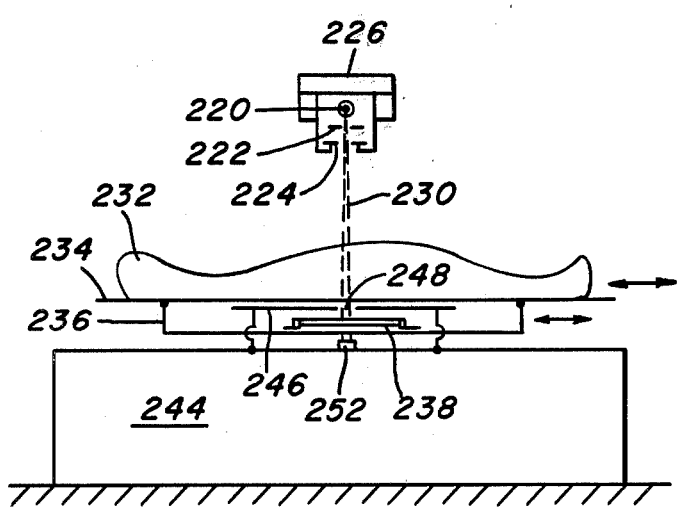
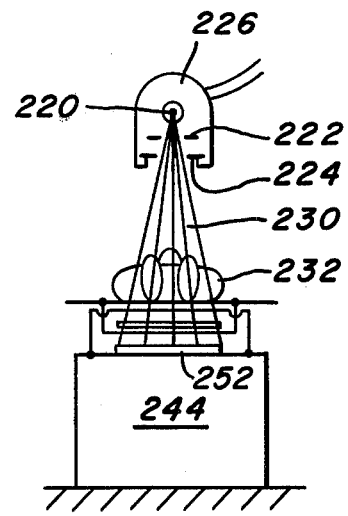
FIG. 13(a).  FIG. 13(b).
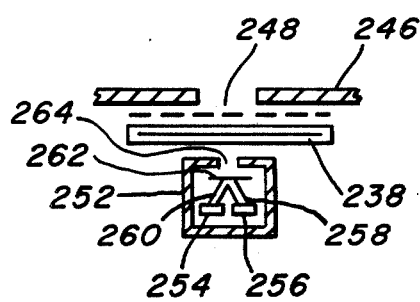
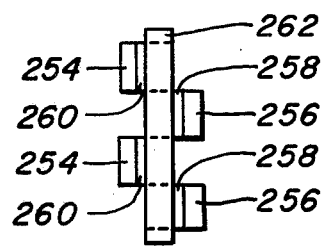
FIG. 14(a).  FIG. 14(b).
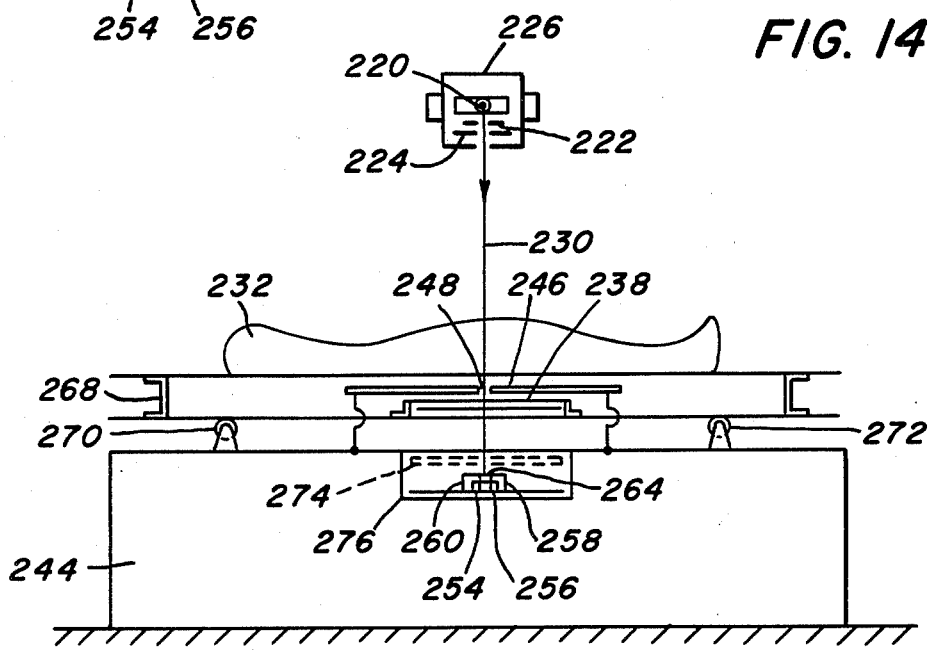
FIG. 15.

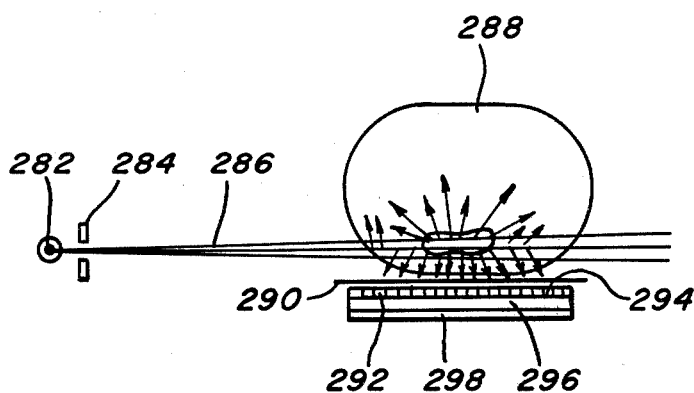
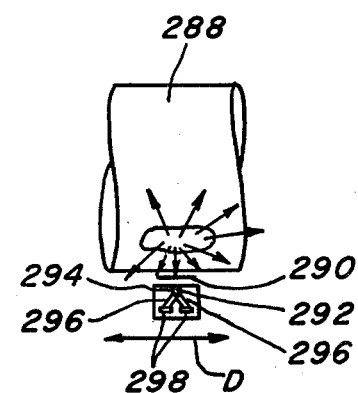
FIG. 16(a).  FIG. 16(b).
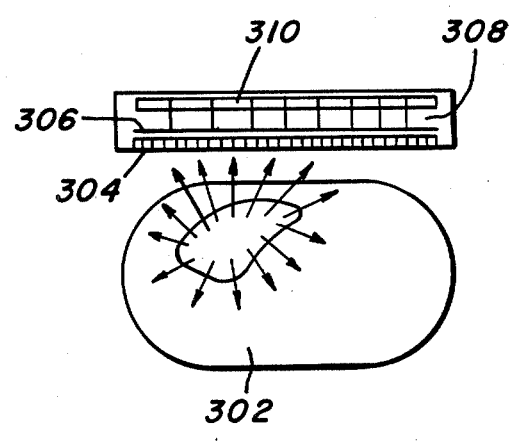
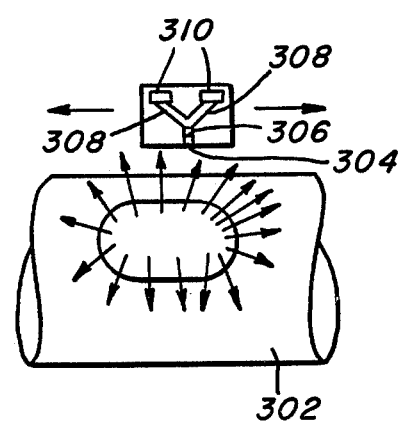
FIG. 17.  FIG. 18.

RADIOGRAPHY APPARATUS

BACKGROUND OF THE INVENTION

1. Field of the Invention

This invention relates to radiography apparatus adapted to provide improved contrast sensitivity while permitting reduced radiation exposure. More specifically, this invention relates to radiography apparatus employing a self-scanning array of photodiodes.

2. Description of the Prior Art

In the use of radiation, such as x-rays, gamma rays and nuclear particles, in view of the potential hazardous effects, means have been provided in order to minimize the morbidity and mortality of radiation exposure. The hazards which result from excessive exposure to radiation exist not only where a patient is being subjected to radiation but also with respect to personnel in the surrounding area. One known means for controlling or reforming an x-ray beam before it reaches an object and also minimizing patient exposure to the radiation is disclosed in U.S. Pat. No. 3,973,127 which relates to x-ray tomography. See also U.S. Pat. Nos. 3,947,689; 3,829,701; 3,934,151 and 3,767,931.

In respect of the desire to reduce the radiation exposure, conflicting objectives are encountered. In general, the clarity of the image and ability to perceive contrast so as to reveal the presence of small departures from the desired condition, e.g. a small tumor, requires meaningful radiation exposure. Mere reduction in radiation exposure tends to contribute to deterioration of perception of contrast and detail in the image.

U.S. Pat. No. 3,866,047 discloses the use of a plurality of pencil beams of radiation which are collimated and converted into light which impinges upon one or more photomultipliers. A computer processes the electrical signals emitted by the photomultipliers. Among the problems with this approach are the severe limitations on resolution imposed by the relatively large size of the photomultipliers and the cost of the same. In addition, an inherent difficulty with photomultipliers is their "after-glow" or noise subsequent to exposure to very high levels of light intensity. This memory effect serves to interfere with the efficiency of the system. In addition, this approach is not readily compatible with existing diagnostic x-ray equipment. Further, the use of a pencil beam increases the exposure time and the heat loading of the x-ray tube. In addition, the support equipment, such as independent amplifiers required for each photomultiplier, further increases the cost and physical mass of the system. U.S. Pat. No. 4,010,370 discloses apparatus for computerized tomography wherein a plurality of individual photomultipliers of photodiodes are used with collimators and scintillation crystals, in order to convert x-ray into light and ultimately into an electrical signal containing the image data. The cumbersome use of individual detector means and the associated processing electronics perpetuates a number of shortcomings of U.S. Pat. No. 3,866,047. See also U.S. Pat. No. 4,010,371. U.S. Pat. No. 4,029,964 discloses a scintillation camera adapted for use in nuclear medicine to receive gamma rays resulting from radioactive disintegrations of the radioisotope administered to a patient. The equipment employs a plurality of photodetectors in the form of photomultipliers tubes which are optically coupled as by light pipes to a scintillation detector.

There remains, therefore, a need for a diagnostic radiography system which is adapted for use with reduced levels of radiation while providing improved images or image data of improved contrast sensitivity and detail. There is a further need for such equipment which is compatible with existing radiography equipment and economical to manufacture and use.

SUMMARY OF THE INVENTION

The apparatus of the present invention has met the above-described need by providing a radiography apparatus wherein the use of a flat, generally rectangular beam or a fan-shaped beam of radiation in combination with collimator means, scintillator means and means for optically coupling a self-scanning array of photodiodes to the scintillator means will permit production of images or image data with high contrast sensitivity and detail. It is contemplated that the self-scanning array of photodiodes may contain from about 60 to 2048, and preferably about 256 to 2048, individual photodiode elements per inch of object width, thereby permitting maximum data collection to produce a complete image or complete collection of image data.

It is an object of this invention to provide radiography apparatus which substantially reduces the amount of radiation to which the patient is exposed while providing an image of desired detail.

It is a further object of the present invention to provide a radiography system which permits improved contrast sensitivity and detail well beyond the limit set by the human eye.

It is another object of this invention to provide radiography equipment which reduces the influence of scattered background radiation upon the image or image data without the long exposure time required by a simple "flying-spot" technique.

It is a further object of the invention to provide such radiography apparatus which is economical to manufacture and operate and is compatible with existing radiography equipment.

It is a further object of this invention to provide such radiography apparatus which is adapted for use in both planar scans, linear tomography and axial tomography.

It is a further object of this invention to provide such apparatus which is adapted to cover wide fields of view which can be imaged with higher contrast sensitivity than is now available through the combination of photographic film with intensifying screens.

It is a further object of this invention to provide such a system which is of relatively low cost and substantially reduced bulk and weight, thereby contributing to increased convenience of usage and storage.

It is a further object of the invention to provide such a system which is adapted for use in nuclear isotope scanning.

It is a further object of this invention to provide such a system wherein direct electronic readout is provided, and objectionable noise is reduced to a minimum level.

It is another object of the invention to permit very low patient exposure consistent with the desired resolution and contrast sensitivity.

These and other objects of the invention will be more fully understood from the following description of the invention on reference to the illustrations appended hereto.

BRIEF DESCRIPTION OF THE DRAWINGS

FIGS. 3(a) and 3(b) are, respectively, front elevational and end elevational views of a modified form of radiography apparatus of the present invention, wherein the radiation generator and collimator means move along an arcuate path with respect to the self-scanning photodiode array.

FIG. 4 is a schematic illustration of an embodiment of the invention wherein a moving shutter is positioned in front of the self-scanning array of photodiodes.

FIG. 5 is a schematic illustration of a form of radiography apparatus of the present invention wherein the scintillator means are positioned on a moving support.

FIGS. 6(a) and 6(b) are schematic illustrations of an embodiment of the invention wherein one or more self-scanning arrays of photodiodes are mounted on a moving support.

FIG. 7 illustrates schematically another embodiment of the invention wherein optical coupling is effected by means of an x-ray image intensifier.

FIGS. 13(a) and 13(b) show, respectively, radiography apparatus of the present invention adapted for use with conventional diagnostic x-ray tables being used for patient examination.

FIGS. 14(a) and 14(b) are partially schematic, cross-sectional and plan illustrations, respectively, of a multiple self-scanning array of linear photodiodes system.

FIG. 15 is an elevational view, partly in section and partly schematic, showing a means of adapting existing patient diagnostic radiography for use with the present invention.

FIGS. 16(a) and 16(b) illustrate schematically, in front and side elevation, respectively, an embodiment of the present invention adapted for use with fluorescent scanning techniques.

FIGS. 17 and 18 illustrate schematically embodiments of the present invention adapted to be used with nuclear isotope medicine.

DESCRIPTION OF THE PREFERRED EMBODIMENTS

As used herein, the term "object" or "test object" or words of similar import will refer to various types of objects through which it is desired to pass radiation for tests or diagnostic purposes including, but not limited to, humans and animals, specimens removed from humans and animals, non-destructive testing and security purposes. While for purposes of clarity of description, specific reference will be made herein to a preferred use in medical environments, it will be appreciated that other forms of objects may be employed in connection with the apparatus of this invention in addition to medical uses and such other uses are expressly contemplated.

As used herein, the terms "self-scanning array of photodiodes", "self-scanning integrated array of photodiodes" and words of similar import shall mean one or more integrated circuit elements having a plurality of photodiodes, each associated with a storage capacitor on which it integrates electrical charges and a multiplex switch for periodic readout by means of an integrated switch register scanning circuit. This term shall expressly include, but not be limited to, linear arrays having about 60 to 2048 (preferably about 256 to 2048) photodiodes per linear inch, and the associated circuitry, as well as planar and rectangular arrays thereof.

As used herein, the term "image information" shall refer to the electrical signals emerging from the self-scanning photodiode array, images or data created through use of said electrical signals, without or with intervening storage or modification thereof, and images created with or without addition to or subtraction from the image data.

Figure 1A:
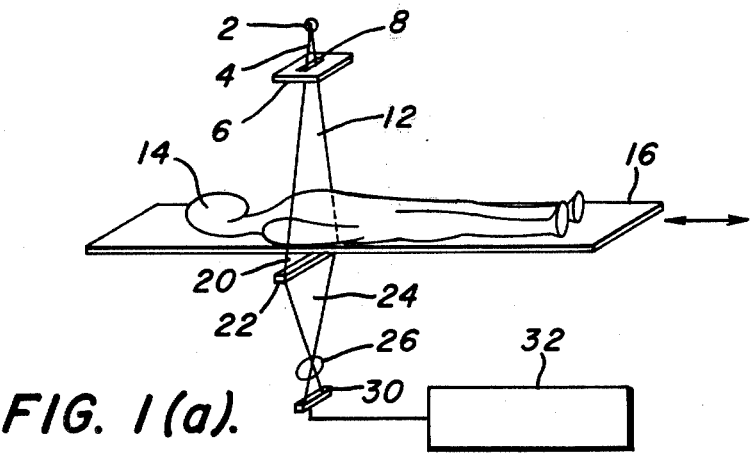
FIG. 1(a) is a schematic illustration of a form of radiography system of the present invention wherein the scintillator means is optically coupled to the self-scanning photodiode array by means of a lens.

Referring now, more specifically, to FIG. 1(a), there is shown a radiation source 2, which, in the form shown, is an x-ray generator. The x-ray generator emits a conical beam of x-ray 4 which impinges upon collimator 6 which is preferably made of lead or other high atomic number material and contains an elongated slit 8 which permits passage of a portion of the conical x-ray beam 4 therethrough. A fan-shaped x-ray beam 12 impinges upon the object 13, which, in the form shown, is a patient. The patient 14 is shown reclining on a movable support table 16 which is adapted to be reciprocated in the directions indicated by the arrows. This permits sequential exposure of various portions of the patient to the fan-shaped x-ray beam 12, while preserving the stationary position of the apparatus apart from the support table 16. Alternatively, if desired, the patient can be maintained stationary and the rest of the apparatus moved relative thereto to achieve the same objective. The portion of the fan-shaped x-ray beam 12 which has passed through the patient has been indicated generally by the reference number 20. It impinges upon scintillator means 22, which, in the form shown, is a relatively narrow phosphor screen. The scintillator means converts the x-ray energy into visible light photons. The beam of light 24 emerging from the scintillator means 22 is, by means of lens 26, caused to impinge upon the self-scanning array of photodiodes 30. The lens 26, therefore, serves as an optical coupling means to cause the light beam 24 to impinge upon the self-scanning photodiode array 30, which, in the form shown, is a linear array. The self-scanning linear array of photodiodes emits electrical signals corresponding to the light which impinges thereon. The electrical signals which contain image information are then delivered to the electrical processing unit 32 which will be described in greater detail below. The electrical processing unit 32 may consist of a digital computer which stores the electrical signals in a memory bank and then, with or without modification thereof, presents the desired image in desired output form, such as by presenting a visual image, a stored image or a computer printout of the data.

If desired, in the form shown in FIG. 1(a), as an alternative, one may keep the patient 14 and x-ray generator 2 stationary and effect relative movement of the collimator 8, scintillator means 22, lens 26 and diode array 30.

Figure 1C:
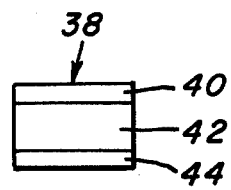
FIG. 1(c) is a schematic illustration of the scintillator-optical coupling-photodiode assembly of FIG. 1(b).
Figure 1B:
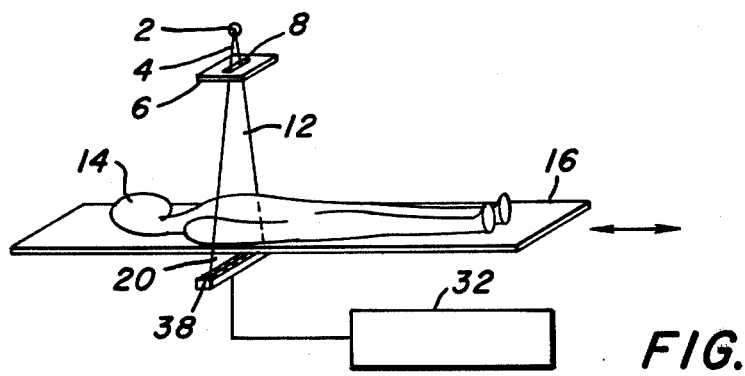
FIG. 1(b) is a schematic illustration similar to FIG. 1(a) except that fiber optic means are employed to optically couple the scintillator means to the self-scanning photodiode array.

Referring now to FIG. 1(b), there is shown a modification of the means for receiving x-ray beam 20 and converting the same to an electrical signal received by the electrical processing unit 32. In the form shown, the scintillator means-optical coupling-self-scanning linear photodiode array assembly 38 accomplishes this function. Referring now to FIG. 1(c), the assembly 38 will be considered in greater detail. It is seen that the scintillator means 40 receive the x-ray beam 20 (not shown in this view) and by means of fiber optic members 42 deliver the light to self-scanning photodiode array 44. An x-ray opaque shield (not shown) is preferably provided around portions of array 44 not in contact with fiber optic members 42 to resist scattered radiation impinging on array 44. Whereas, in the embodiment shown in FIG. 1(a), the phosphor screen 22 was longer than the self-scanning photodiode array 30, and the lens 26 served the function of converting the light beam 24 to a beam which would fall within the linear extent of the self-scanning photodiode array 30, in the present form of FIG. 1(b), the self-scanning photodiode array 44 is generally coextensive in dimension with the scintillator means 40, which, in this form, is a phosphor screen and is provided with optical coupling by means of the fiber optic members 42 which are substantially coextensive with the scintillator means 40 and array 44.

Figure 2:
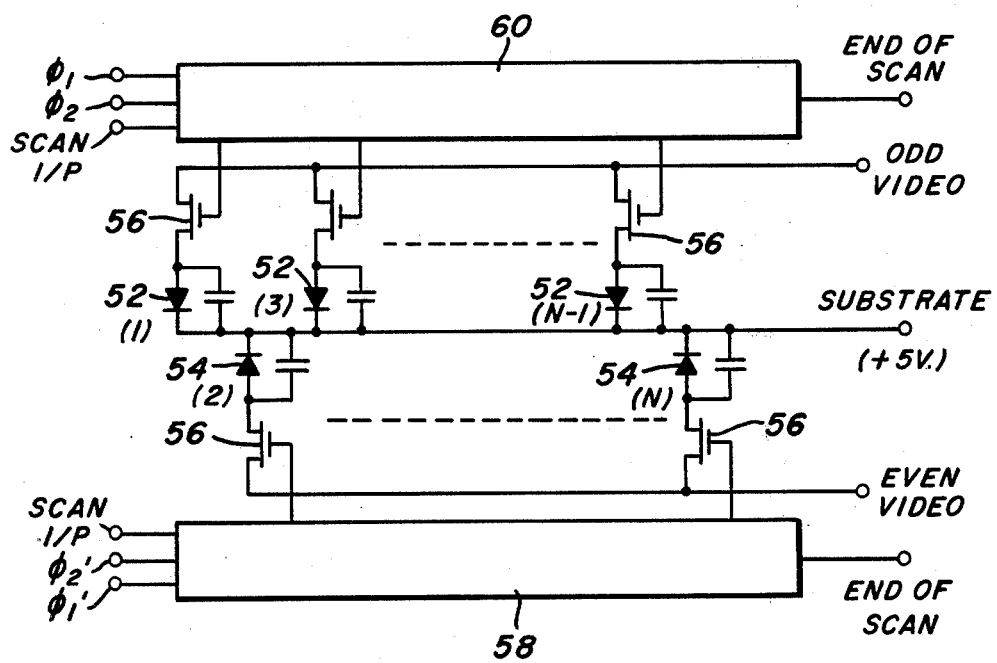
FIG. 2 is a diagram of a form of self-scanning photodiode array which is adapted for use in the radiography apparatus of the present invention.

Before discussing FIG. 2, a general background on self-scanning photodiode arrays will be provided. In the self-scanning photodiode array, small integrated circuit switches are connected to each of the collector electrodes arranged in a row. These switches can connect each individual collector to a common video line on command, so that a series of electrical output signals appear at the end of line of photodiodes, each representing the amount of charge that has been accumulated during the exposure to light.

In normal operation of such a device, the individual diode acting like a very small electrical capacitor is charged up to a certain potential. The photons falling on each photodiode cause electrical conduction to take place, discharging some of the initial potential. The number of charge carriers is directly proportional to the number of photons incident on each photodiode, and the charge generated is stored by the capacitance of the photodiode during the exposure period.

In the readout cycle, a solid-state switch is activated and suddenly dumps the charge into the common video signal line connected to the output of a preamplifier. The switching is accomplished by a pair of digital shift registers on the semiconductor chip in such a way that when a pulse is applied to the first element of the register, the first switch is closed. At the next pulse, this next switch is closed, every pulse causing the next element of the register to be actuated so as to close the next switch.

All the necessary circuitry is included on the chip making a completely self-scanning device in the sense that the successive actuation of the input to the shift register enables one to interrogate sequentially all of the hundreds of diodes on the chip, much like an electron beam scanning across the picture elements of a television camera tube reads out the charges in the sequential fashion.

The great advantage of the self-scanning photodiode array, aside from its small size, is that each picture element can store a much larger number of charges than a picture element on a television camera target. Thus, typical devices available can store about ten electronic charges before they saturate, allowing a quantum-limited signal to noise ratio of about $(10^7)^{\frac{1}{2}}$ or about 3000 to 1 due to fluctuation in the number of charges per picture element. If one, therefore, arranges matters in such a way that each absorbent x-ray releases about one to ten electrical charges in the photodiode, dynamic ranges of about 1000 to 1 in x-ray exposure can be registered with these devices.

By contrast, typical image orthicons, isocons and other similar T.V. cameras can store only about $10^4$ to $10^5$ electronic charges per picture element, so that the maximum signal to noise ratio or dynamic range possible is about 300 to 1, not much larger than that of film, which is about 100 to 1 for a one millimeter square area at the patient.

Another advantage of these devices is their high efficiency for registering visible photons, which is close to 100%. On the other hand, typical photoelectric surfaces, as used in image intensifiers and television cameras, can be made with only about 10-20% quantum efficiency, giving the solid-state devices an advantage in speed of about five to ten times.

The diode arrays are available with spacings from anywhere from about 60 to 2000 photodiodes per inch and with widths of from about 0.0006 inch to 0.030 inch mounted in ceramic housings typically about 0.100 inch thick and anywhere from about 1 to 1.5 inch along with a width of about 0.400 inch. Thus, they can be placed into a relatively thin package compatible with the thickness of present film-screen cassettes.

Referring now to FIG. 2, there is shown a self-scanning array of photodiodes which consists of a series of odd numbered photodiodes 52 shown as numbering from (1) through (N-1) and a series of even numbered photodiodes 54 shown as numbering from (2) through (N). Each photodiode 52, 54 is associated with a storage capacitor on which it integrates electric current and a multiplex switch 56 for periodic readout by way of its associated integrated shift register scanning circuit 58, 60. The number of photodiodes 52, 54 which may be provided in the self-scanning array may, for example, consist of about 60 to 2048 in a relatively small space. For example, the photodiodes 52, 54 may be positioned on 0.001 inch centers. Such dimensioning would permit the use of 1000 photodiodes per linear inch of self-scanning photodiode array. As a result of this large number of photodiodes in the context of the integrated circuit array, there is no need for externally positioned electrical equipment for each separate photodiode to assist with conversion of the impinging light into a corresponding electrical signal. This permits a high degree of retention of image information with resultant high degree of spatial resolution, contrast sensitivity and dynamic range.

In the self-scanning photodiode array shown in FIG. 2, each shift register 58, 60 accesses alternate diodes and connects them into one of the two output lines alternately. By clocking the two registers in parallel, two parallel signal pulse streams may be obtained from the two outputs but representing odd numbered diodes 52 and even numbered diodes 54, respectively. Alternatively, the two output terminals could be connected in parallel, and the registers clocked alternately. One signal stream is then obtained representing each diode 52, 54 in the array. Numerous types of self-scanning integrated circuits of photodiode arrays may be advantageously employed in the apparatus of the present invention. For example, the self-scanning photodiode arrays sold by Integrated Photomatrix, Inc. of Mountainside, N.J., under the trademark IPI (M Series) or those sold under the trademark RETICON by Reticon Corporation, 910 Benicia Avenue, Sunnyvale, Calif. 94086, may be employed. Charge coupled photodiode arrays may also be employed advantageously. While not disclosing any reference to use of the equipment in connection with x-ray gamma ray or nuclear particle radiography techniques, additional information regarding self-scanning photodiode arrays and related technology may be obtained from an article entitled "Self-Scanning Photodiode Arrays for Spectroscopy", *Research-Development,* April, 1976 and the following U.S. Pat. Nos. 3,822,362; 3,717,770; 3,993,888; 3,947,630; 3,919,468; 3,801,820; 3,935,446; 3,993,897; 3,936,630; 3,955,082 and 3,755,678, for example.

Considering further the scintillator means 22, in the form shown in FIG. 1(a), a phosphor screen was employed to convert that portion of the x-ray beam which had passed through the object 14 into visible light which corresponds to the intensity and distribution of the impinging x-ray beam. As diagnostic range x-rays generally fall into the photon energy range of about 10 to 150 KeV and have a wave length of about 0.12 to 0.008 nanometers and the coefficient of absorption or absorption efficiency of a self-scanning silicon photodiode array is poor in this range, it is preferable to employ the scintillator means of the present invention, as the absorption coefficient of silicon for light in the corresponding range of 400 to 800 nanometers is very good and may exceed 95%. The scintillator means of the present invention may consist of a thin, single crystal of a material such as bismuth germanate which is capable of absorbing approximately 90% of x-rays in the 10 to 150 KeV energy range. The scintillator means may also consist of powdered or evaporated crystals of gadolinium oxysulfide on a suitable x-ray transparent backing. A preferred form of scintillator means for use with high energy x-rays (about 50 to 150 KeV) or gamma rays (about 50 to 1000 KeV) is a mosaic of thin, single crystals in the form of fibers or thin sheets that are optically isolated from each other. This permits the mosaic to be made thick in the direction of the incident radiation so as to absorb the radiation with the greatest possible efficiency without meaningful loss of spatial detail. A mosaic of scintillation crystals separated by thin sheets of a heavy metal (such as tantalum, tungsten or lead), designed to minimize x-ray scattering from one crystal to its neighbors, may advantageously be employed. Another suitable scintillator means is a fluorescent screen. A rare earth oxide (such as gadolinium oxysulfide, for example) screen may advantageously be employed as scintillator means. An important characteristic of the scintillator means is that x-ray photons will be absorbed without significant loss of detail. Other forms of scintillator means which may advantageously be employed would be an x-ray image intensifier tube or a solid-state intensifying panel.

Referring now to FIGS. 3(a) and 3(b), there is shown an embodiment of the invention wherein the radiation generating means and collimating means rotate along the predetermined path, preferably about an axis at or closely adjacent to the self-scanning array of photodiodes. The x-ray generator 66 may be mounted on an arm for rotational movement to a position, such as that indicated by the reference number 66'. If desired, conventional means may be provided on the arms supporting the x-ray generators 66 so as to provide an indication of relative position of the x-ray generator 66 on its curved path. Collimator means 68, 70 serve to convert the conical x-ray beam into a fan-shaped beam, such as 72, which impinges upon the patient 76 and provides beam 74 which impinges upon scintillator means 78 and is converted into visible light, which, by means of light coupling means, such as fiber optics 80, is transmitted to the self-scanning array of photodiodes 82. The use of a fan beam contributes to desired rejection of scattered radiation. It will be appreciated that by sequentially moving the x-ray generator 66 along the curved path, a series of images similar to those provided by the system shown in FIG. 1 (b) will be established.

It is noted that in this embodiment both the patient 76 and the combination scintillator means 78-optical coupling means 80-self-scanning array of photodiodes 82 are stationary while the x-ray generator 66 and collimator means 68, 70 rotate. Also, the collimator means 68, 70 remain at the same relative position with respect to the x-ray generator 66.

Referring now to FIGS. 4, 5 6(a) and 6(b), several embodiments employing a large fixed phosphor screen or a long thin strip as scintillator means are shown. A fixed lens is employed as the optical coupling means which serves to reduce the image size so that a smaller array of self-scanning photodiodes can be employed. In addition to or in lieu of use of the simple lens, a reflecting mirror plus lens system could be employed. For example, a linear array of self-scanning photodiodes, one inch in length containing about 60 to 2048 photodiode elements in a row might well be employed for a field of view from about six inches to fourteen inches across.

In the form shown in FIG. 4, two collimators may be employed. A radiation source 88 is positioned adjacent to a moving slit collimator 90. The fan-shaped beam 106 passes through the object 92 and impinges upon scintillator means 94, which, in the form shown, is a fluorescent screen. The primary x-ray photons are converted to light photons which emerge as light beam 108. The light beam, by means of the lens 96, is caused to pass through an opening in the slit moving collimator 98 and impinge upon several horizontally oriented, generally parallel linear arrays defining a planar array 100. Means (not shown) are provided for coordinating the oppositely directed movement of the slit collimator 90 and the moving shutter 98 so as to cause the light beam 110 to be sequentially displaced corresponding to sequential displacement of the fan-shaped x-ray beam 106 through movement of collimator 90 so as to remain incident on the photodiode array 100. It will be appreciated that in FIG. 4 the linear extent, i.e. the depth in the direction looking into the page, of the fluorescent screen 94 may be substantially greater than the length of the self-scanning array of photodiodes 100 with the lens 96 serving to establish the desired minification of the light beam so as to effect proper placement on the photodiode array 100.

In the form shown in FIG. 5, the system has been modified as compared with FIG. 4 in order to provide a relatively small scintillator means 116 in the form of a fluorescent strip which is mounted on a movable support 118 and to delete collimator 98. As a result of the movement of the support 118 being coordinated with the movement in the same direction of the slit collimator 90, the primary x-ray beam 106 will always impinge upon the fluorescent strip 116 which, in turn, will emit visible light photons, which, by means of lens 96, will be caused to impinge upon the self-scanning array of photodiodes.

In the embodiments of FIGS. 4 and 5 the x-ray generator 88, the object 92 and the self-scanning array of photodiodes 100, as well as the lens 96, are all maintained stationary. In the embodiment of FIGS. 6(a) and 6(b), the self-scanning array of photodiodes 124 is mounted upon a movable support 126, the motion of which is coordinated with the movement of slit collimator 90. As a result, the photodiode array 124 will always be in proper position to receive the light beam 110. Also shown in FIG. 6(b) is the use of three collimators 90, 108, 112 in order to provide for improved control of beams 106, 110. In the embodiment of FIG. 6(b), the second collimator 108 is substantially coextensive with scintillator means 94 and is positioned between object 92 and scintillator means 94, thereby serving as a second x-ray collimator. Also, light collimator 112 is placed in front of self-scanning diode array 124 which is mounted on movable support 126. Elements 112, 124, 126 are moved as a unit in synchronous fashion with respect to collimators 90, 108. It will be appreciated that in FIG. 6(a) only collimator 90 is employed, and in FIG. 6(b) two additional collimators 108, 112 are shown, but only one of these collimators 108, 112 could be used in combination with movable collimator 90, if desired. Also, if desired, second and/or third collimators could be employed advantageously with other embodiments of the invention. The additional collimators serve to minimize the influence of scattered radiation and scattered light.

While for purposes of convenience of reference herein, examples have been given of linear self-scanning photodiode arrays, i.e. a single such array which is elongated, it will be appreciated that additional linear arrays may be employed, positioned in relative end-to-end orientation with respect to each other. Also, where it is desired to cover a larger area in a shorter time, two or more parallel lines of linear arrays of self-scanning photodiodes may be employed.

Referring now to FIG. 7, there is shown an embodiment of the invention which, while not preferred, may advantageously be employed in systems wherein a small field size, such as a disc of about nine inch diameter, for example, is involved. In this embodiment, an x-ray image intensifier 132 is employed as the scintillator and optical coupling means. The x-ray beam 144 which has passed through the object 92 impinges upon screen 134 which typically is composed of cesium iodide and an efficient photoelectron emitter which converts the x-ray beam 144 into an electron beam 136 which is caused to impinge upon the self-scanning array of photodiodes 140 by means of magnetic deflection coil 138. The electrical output signals from the self-scanning array of photodiodes 140 is then delivered to the electrical processing unit 32. Alternately, if desired, the arrays of photodiodes could be optically coupled to the image intensifier.

Figure 8:
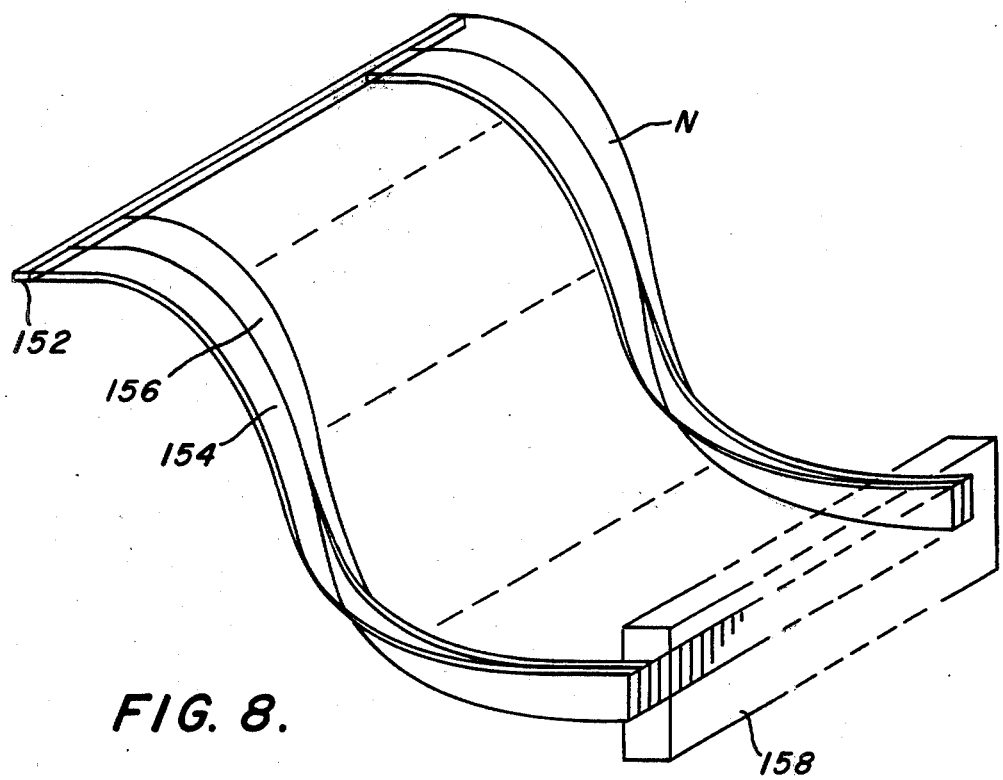
FIG. 8 is a schematic illustration showing optical coupling effected by means of flexible fiber optics.

Referring now to FIG. 8, the use of light pipes or fiber optics means to deliver light from the scintillator means 152 to the self-scanning array of photodiodes 158 is illustrated. While the fiber optics may be of any size so as to properly correspond to both size of scintillator means and size of self-scanning array of photodiodes, in the form shown, the scintillator means is in the form of an elongated scintillator strip or mosaic, and the photodiode means is of lesser longitudinal extent. As a result, the light pipes or fiber optic bundles 154, 156 through N are relatively thin and flexible. The light received by light pipe 154 is received from a portion of the scintillator means 156 equal to the full width of the light pipe 154 and, as a result of its being twisted, the light is delivered to a portion of the self-scanning photodiode array which is equal to the thickness of the light pipe 154. As a result, a longitudinal unit of the scintillator means 152 equal to light pipe width is delivered to a corresponding sector of the self-scanning photodiode array 158 equal to the lesser thickness of the light pipe 154. The twisted light pipes or guides may conveniently consist of flexible light pipes or fiber optic bundles composed of plastic or glass. As a result of the geometric dimension reduction shown in FIG. 8, an array of photodiode detectors, consisting of 1000 elements with the photodiode centers being at one mil center-to-center spacing and having a width of 17 mils, the scintillator may be 17 inches long and coupled to the photodiode array only one inch in length, for example. The light pipes can be made one mil by 17 mils with 1000 of them being provided, i.e. one for each photodiode sensor. Alternatively, the light pipes may be tapered so as to allow the use of scintillator elements wider than one mil.

An advantage of the use of full scale fiber optic coupled arrays such as that shown in FIG. 1(c) is the capability of delivering large quantities of light to the array when it is desired to reduce patient exposure.

Another advantage of the embodiment of FIG. 8 is that the arrangement permits for shielding means (not shown) to be provided around the self-scanning photodiode array 152 so as to shield the array from any stray radiation.

Figure 9:
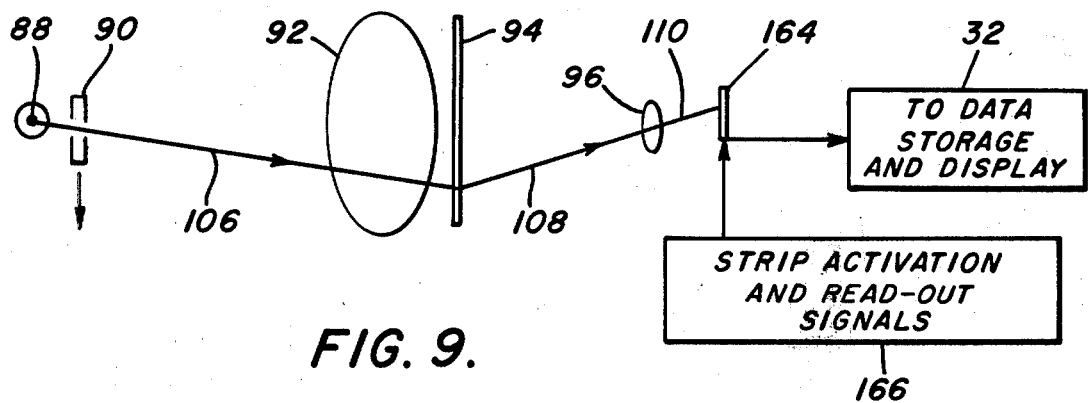
FIG. 9 illustrates schematically a form of optical coupling of the scintillator means to the self-scanning photodiode array by means of a lens.

Referring now to FIG. 9, the embodiment shown in this figure contemplates the use of a planar array (i.e., an array having a number of parallel linear arrays of photodiodes rather than a single line of photodiodes) and electrical switching of the self-scanning photodiode array as a substitute for a second mechanical movement coordinated with movement of the slit collimator 90. In this embodiment, the signal produced by the light beam 110 (corresponding to the primary radiation beam 106), which impinges upon the self-scanning array of photodiodes, will be received by only the row or rows of sensors activated by electrical control means 166, and responsive electrical signals will be emitted to signal processing means 32 as previously discussed. The array of self-scanning photodiodes 164 in the present embodiment may consist of a genrally rectangular array having a number of parallel, linear arrays disposed closely adjacent to each other. As the light beam 110 is subjected to relative vertical displacement as a result of movement of the slit collimator 90, the electrical control means 166 will cause the recording of the signals only from the particular array or arrays on which the light generated by the primary radiation beam 106 impinges. This embodiment offers the advantage of minimizing the number of components of the apparatus which must be moved mechanically, and also permits rejection of scattered radiation by discharging the photodiodes of any row just before the row is reached by the primary beam.

Figure 10:
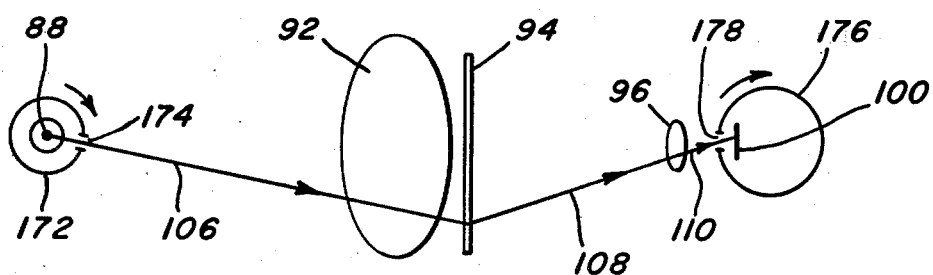
FIG. 10 illustrates another embodiment of the present invention wherein rotating, hollow cylinders coordinate release of radiation and receipt of radiation from the radiation generator and receipt of light by the self-scanning array of photodiodes.

Referring now to FIG. 10, a further embodiment of the invention wherein mechanical means are employed to coordinate creation of the fan-shaped x-ray beam 106 and exposure of the self-scanning array of photodiodes 100 (which may be a linear or rectangular array) to light beam 110 will be discussed. In this embodiment, the collimator 172 takes the form of a hollow cylinder composed of a radio-opaque material having a longitudinally oriented slit 174. The cylinder is adapted to rotate or oscillate about its longitudinal axis and to sequentially create the fan-shaped x-ray beam 106 and move it along the object 92. If desired, the x-ray tube 88 may be pulsed when the slit 174 is in the desired position. A shield member 176 is mounted for synchronous rotation or oscillation with the collimator 172 and has a corresponding elongated slit 178 which permits the light beam 110 to impinge upon the self-scanning array of photodiodes. The shield 176 is preferably composed of a radio-opaque material. Rotation of collimator 172 is synchronized with the rotation of shield member 176 by any suitable means, such as mechanical synchronization, by gear means operatively associated with a drive motor or electrical synchronization of a pair of drive motors driving collimator 172 and shield member 176.

Figure 11:
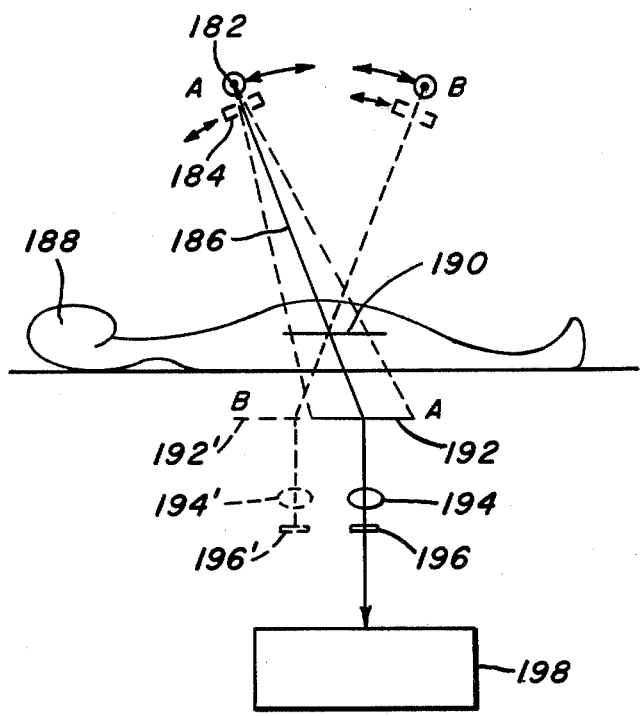
FIG. 11 illustrates an embodiment of the invention adapted to be employed in planar tomography.

Referring now to FIG. 11, there is shown another embodiment of the invention suitable for use as a substitute for x-ray film. In this embodiment of the invention, the x-ray generator 182 and slit collimator means 184 are adapted to be rotated as a unit, such as from position A to position B, shown at the upper portion of FIG. 11. The fan-shaped x-ray beam passes through the patient 188 with 190 being employed to represent the plane of the section being imaged. The rays which pass through the patient 188 impinge upon fluorescent screen 192 which in position A has its light output coupled by means of lens 194 to the multiple row, planar self-scanning array of photodiodes 196. It will be appreciated that this embodiment involves the patient 188 being stationary, while the scintillator means 192, lens 194, self-scanning photodiode array 196 move in coordinated fashion with respect to the x-ray generator 182 and the collimator 184. The electrical output of the self-scanning array of photodiodes 196 is delivered to signal processing means 198. When the x-ray generator 182 is in position B, the fluorescent screen 192', lens 194' and self-scanning photodiode array 196' will be in the position shown toward the lower left of FIG. 11, with the means connecting the photodiode array 196' to the signal processing means 198 (not shown in this view). This embodiment presents the ability to achieve higher image quality than would be the case with present fast filmscreen combinations and provides for greater ability to detect small contrast differences. In addition, electrically stored images are immediately available. It will be appreciated that when the x-ray generator 182 is at a fixed position (such as position A, for example), the collimator 184 will be subjected to relative movement as indicated by the arrows in order to provide a full scan at position A. Similar procedures are followed at other positions. Further, the inherent contrast is increased in respect of present film techniques through reduced detection of scattered radiation. This embodiment also permits precision subtraction of successive tomographic images so as to allow visualization of blood vessels, tumors and other anatomical features.

Figure 12A:
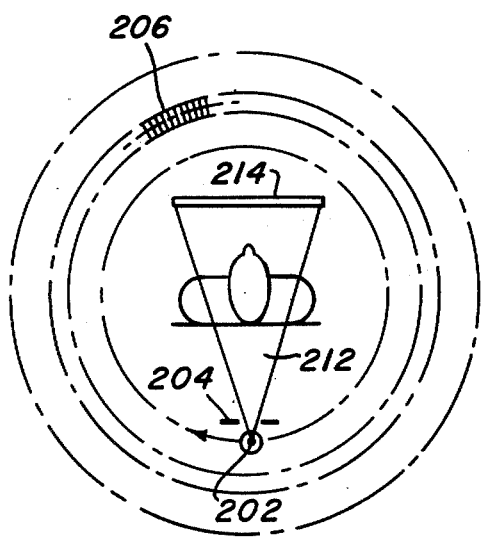
FIG. 12(a) illustrates schematically an embodiment of the invention adapted to be employed in computerized axial tomography.
Figure 12B:
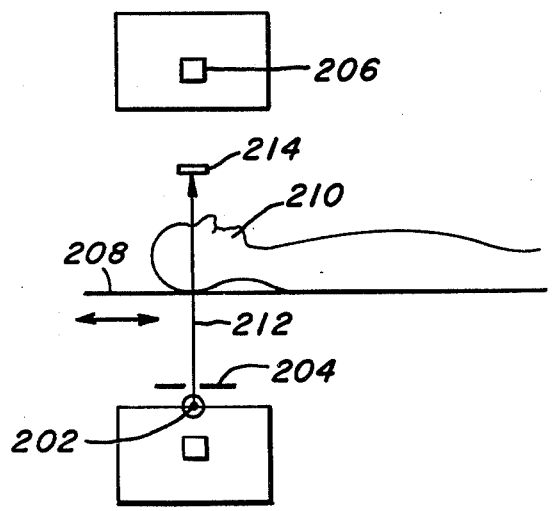
FIG. 12(b) illustrates schematically an embodiment similar to that of FIG. 12(a) except that the system is used generally perpendicularly to the line of view of FIG. 12(a).

Referring to FIGS. 12(a) and 12(b), an embodiment of the invention which is compatible with existing computerized axial tomographic scanners (CAT scanners) will now be considered. As is shown in these figures, an x-ray generator 202 cooperates with a slit collimator 204 to define a fan-shaped x-ray beam which passes through patient 210 supported by axially movable table 208. In one form of conventional computerized axial tomography, the portion of the x-ray passing through the patient would then impinge upon the array of detectors 206, which have been shown schematically in these figures. The x-ray generator 202, collimator 204 and detector means 206 are adapted for synchronized orbital movement about an axis passing through the patient 210. This embodiment of the present invention contemplates insertion of a combination scintillator-optical coupling-self-scanning array of photodiodes 214 on the exit side of the patient 210. If desired, the combination scintillator-optical coupling means-self-scanning array of photodiodes may take the form of that shown in FIG. 1(c). By providing the combination 214, existing CAT scanner equipment is converted to a linear scanner by simply moving the patient underneath the combination 214. This permits an entirely new means for detecting low density differences and much finer spatial detail indicating lesions or abnormalities to the clinician far in excess of that available by means of a series of plane films and without waiting for film development. It also permits greatly enhanced use of the existing CAT scanners without the need to acquire a new x-ray source and patient table. The combination 214 may readily be moved out of the way when not in use and, therefore, will not interfere with the normal mode of present CAT scanner operation. It is further contemplated that the combination 214 may be movable around the patient so that any desired view may be obtained.

Referring now to FIGS. 13(a), 13(b), 14(a) and 14(b), another embodiment of the invention will be considered. This embodiment illustrates another form of adaptability of the present invention to use with conventional equipment. In this embodiment, a self-scanning photodiode assembly may be employed in lieu of or in addition to conventional x-ray film-screen cassettes. In this embodiment, a fixed overhead x-ray generator 220 is associated with a pair of slit shutters 222, 224 and emits fan-shaped x-ray beam 230. The x-ray apparatus is enclosed within housing 226. The fan-shaped x-ray beam 230 impinges upon patient 232 which is supported by and adapted to move with tabletop 234 in the direction indicated by the arrows. Underlying and fixedly secured to tabletop 234 and adapted for movement therewith is support member 236 which contains x-ray film-screen cassette 238. This provides for exposure of the conventional x-ray cassette sequentially as the patient and cassette move under the fixed fan-shaped x-ray beam 230. Base 244 supports stationary x-ray shutter 246 which is provided with an elongated slit 248 through which the fan-shaped beam 230 passes after passing through the patient 232. As the shutter 246 is stationary, and the film-screen cassette 238 and patient are subjected to synchronized movement, the film-screen cassette will be sequentially exposed to the x-ray passing through slit 248.

As is shown in FIGS. 14(a) and 14(b), also fixedly mounted with respect to base 244 is the enclosure 252 which contains a pair of self-scanning photodiode arrays 254, 256 which are coupled, respectively, by fiber optic tubes 260, 258 to a single long strip of scintillator means 262. X-ray passing through slit 248 of shutter 246 will pass through opening 264 in enclosure 252 and impinge upon the scintillator means 262 with the light emitted by the scintillator means being delivered to the self-scanning photodiode arrays 254, 256 by fiber optic means 260, 258. As is shown in FIG. 14(b), in this embodiment the self-scanning photodiode arrays 254, 256 are positioned in staggered fashion and are optically coupled to scintillator means 262 to provide continuous receipt of light emerging from the scintillator means by the arrays 254, 256. Alternate light pipes provide light to alternate photodiode arrays from alternate sections of the scintillator means 262. As a result, this system permits taking of both permanent picture, conventional x-rays and the collection of image information contemplated by the present invention simultaneously or sequentially. While the self-scanning photodiode array system will function more efficiently without the presence of the film-screen cassette, it should be appreciated that even with the best x-ray screens, approximately 40–50% of the primary x-ray beam will penetrate to the scintillator means 264.

This embodiment provides a number of advantages in addition to permitting the taking of conventional x-rays coupled with the use of the self-scanning photodiode array of the present invention simultaneously. Only slight modification to standard diagnostic tables and overhead x-ray tubes are required in order to employ this system. In addition, the x-ray shuttering system is stationary and can be quite massive. The system permits employing high energy x-rays with resultant dose reduction being permitted. The effect of scattered radiation is reduced, and the spatial resolution is improved as the effective focal spot size is at a minimum with respect to the plane of the fan-shaped beam 230.

With existing table motion speeds of approximately three inches per second, effective exposure times per line would be only 0.005 seconds. With an increase in table speed to ten inches per second, coronary arteries only two inches long could be scanned in 0.2 seconds with effective exposure length of only about 0.0002 seconds.

Referring now to FIG. 15, a generally similar system to that shown in FIGS. 13(a) and 13(b) will be considered. In this form the standard ion chamber 274 and Bucky tray 276 are retained in position. The ion chamber 274 serves to monitor beam intensity during exposure. It may also be employed as a means for aligning the overhead x-ray generator 220 with slit 248. Also, a variable speed motor may be employed to drive the table and be controlled by a signal derived from the ion chamber in order that one can move the patient 232 more slowly through regions of high density and more rapidly through regions of low density. In the alternative, one may adjust beam current to keep a constant average output of the ion chamber. The ion chamber may also serve as a safety feature by being set to shut off x-rays after a certain predetermined charge has been accumulated.

While fiber optic means have been shown as the basis for optical coupling in the embodiments shown in FIGS. 14(a), 14(b) and 15, it will be appreciated that other forms of optical coupling, such as, for example, those expressly disclosed herein or other appropriate means may be employed.

Referring now to FIGS. 16(a) and 16(b), application of the present invention to so-called fluorescent scanning will be considered. In such a procedure, a collimated x-ray beam impinges upon the object, such as a patient, and excites the fluorescent radiation in the object. In the form illustrated, x-ray generator 282 cooperates with collimator 284 to provide a fan beam 286 of x-ray which impinges upon object 288. The detector system, in the form shown, is oriented generally perpendicularly with respect to the fan beam 286. Relative movement is established between object 288 and the x-ray generator 282 and collimator 284 to establish a direction of scan such as that illustrated by the double-headed arrow "D" in FIG. 16(b). An x-ray filter 290 is interposed between the object 288 and the detector system. This filter serves to remove radiation having K-absorption edges above and below the characteristic trace element, such as iodine, for example. After the characteristic x-ray radiation emitted by the object, such as iodine in the thyroid, for example, passes through filter 290 and collimator 292 having fine collimating slits, it then impinges upon scintillator mosaic 294. The light output from the scintillator mosaic 294 is optically coupled to a self-scanning array of photodiodes 298 by optical coupling means 296, such as fiber optic means.

The advantages of the embodiment shown in FIGS. 16(a) and 16(b) over more conventional practice are the ability to handle many more picture elements simultaneously than would be possible with a single small detector, the ability to respond to low energy x-ray radiation that cannot be recorded by widely used gamma cameras. In addition, it provides much higher spatial resolution, and it is easy to shield the detector strip from stray background radiation. While not shown, it will be appreciated that the self-scanning array of photodiodes will generally be housed within an x-ray opaque or gamma ray opaque housing except for that portion of the array which is intended to be optically coupled to the scintillator means. The dosage of radiation to the patient is also reduced by comparison with present isotope studies.

Referring now to FIGS. 17 and 18, application of the present invention to nuclear medicine will now be considered. In this embodiment, the object 302 becomes, generally through injection or oral consumption of a radioactive isotope (such as radioactive iodine), the source of radiation which is generally a gamma ray emitting isotope. The emerging radiation passes from the exit side of object 302 through collimator 304 and impinges upon scintillator 306 from which it is transported as visible light photons by means of fiber optics 308 to the staggered self-scanning arrays of photodiodes 310.

Figure 19:
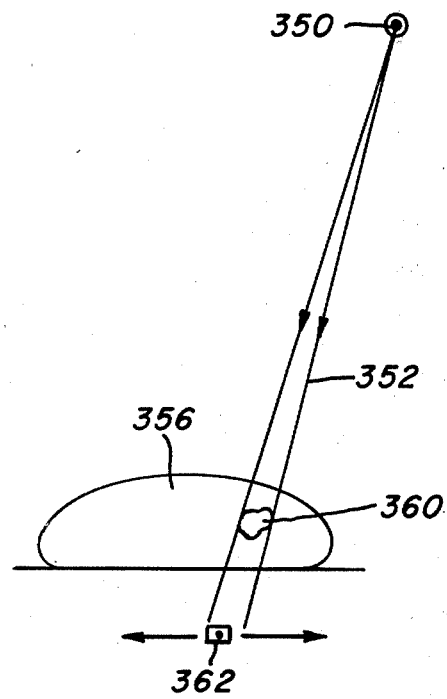
FIGS. 19 and 20 illustrate schematically embodiments of the invention adapted to be used in monitoring radiation therapy.
Figure 20:
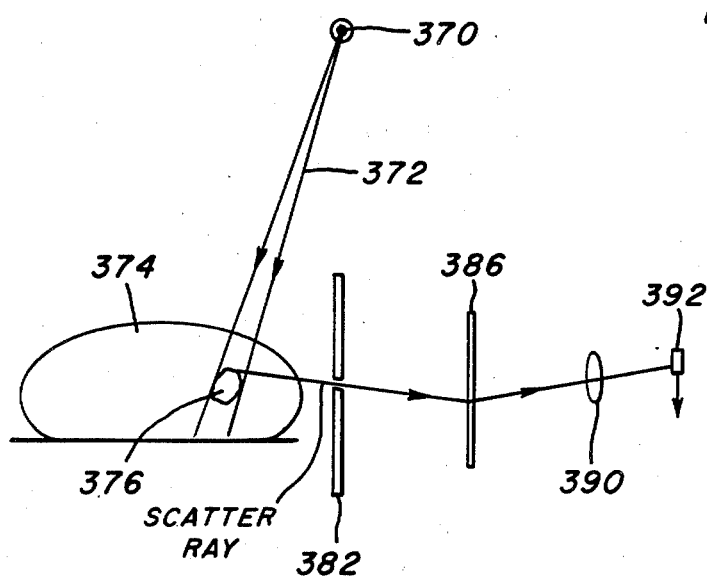

FIGS. 19 and 20 illustrate two embodiments of the invention adapted to be used as an adjunct to therapy to monitor the effectiveness. In FIG. 19 a radiation source 350 emits a beam of radiation 352 which impinges upon patient 356 and passes through tumor 360. The portion of the beam emerging from the exit side of patient 356 is received by assembly 362 which may consist of a scintillator, optical coupling means and self-scanning array of photodiodes, as shown in FIG. 1(c). The assembly 362 is reciprocated in the direction indicated by the arrows in order to sequentially expose the assembly 362 to different portions of the radiation.

In the form shown in FIG. 20, the radiation source 370 emits beam 372 which enters patient 374 and passes through tumor 376. Scattered radiation passes through slit collimator 382 and impinges on scintillator 386. The resultant light beam is directed by lens 390 to self-scanning photodiode array 392 which is adapted to be reciprocated in a vertical direction.

Figure 21:
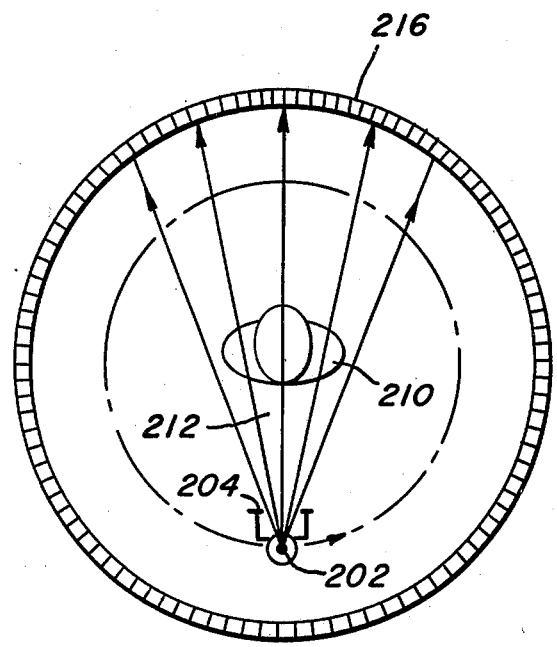
FIGS. 21 and 22 illustrate schematically embodiments of the invention adapted for use with computerized axial tomography.
Figure 22:
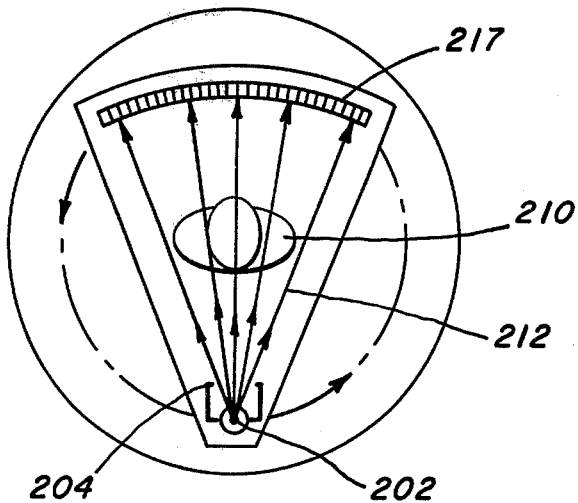

Referring now to FIGS. 21 and 22, there are shown other embodiments of the invention applicable to Computerized Axial Tomography scanners (CAT scanners). In these embodiments, the conventional individual large area scintillators and photomultipliers or other detectors of existing fan-beam type of CAT scanners are replaced by the present combination of scintillator and self-scanning integrated photodiode arrays of very high spatial resolution. Specifically, the substitution of self-scanning detector assemblies, such as shown in FIG. 1(c), leads to advantages over existing xenon gas or separate scintillator-photomultiplier detectors. First, it allows one to achieve in the same apparatus both fine detail images of the planar type and coarser images of sections of the body without the need for a separate attachment 214 shown in FIGS. 12(a) and 12(b). Also, it allows one to obtain much finer detail for sectional views produced by CAT scanners. This cannot be done in present CAT scanners, which are generally limited in the spatial resolution they can achieve by the size of their individual detectors, typically about two to three mm, for example. Thus, it would be technically and economically totally unfeasible to provide for some 8000 separate scintillator and photomultiplier assemblies that would be needed to achieve a detector element size of 0.5 mm in the system shown in FIG. 20 or 16,000 such separate assemblies if a detail resolution of ¼ mm were desired, comparable to that of present fast film-screen combinations.

In the form shown in FIG. 21, the radiation source 202 emits a beam of radiation which is converted into fan beam 212 by collimator means 204 and passes through patient 210. The beam then impinges upon the assembly 216 consisting of scintillator means, optical coupling means and self-scanning array of photodiodes. This assembly may conveniently be composed of elements such as those shown in FIG. 1(c). The scintillator means may take the form of small strips having a ¼ mm by ¼ mm by ¼ mm size. The assembly 216 in this embodiment is presented in the form of a stationary circular assembly. In this fashion, orbital movement of the radiation source 202 along the broken circle will permit patient exposure over a 360 degree range. In the form shown, the axis of rotation of the radiation source 202 passes through the patient 210.

In the form shown in FIG. 22, the assembly 217 consists of an arc-like sector which is adapted to rotate or oscillate in synchronous fashion with respect to the radiation source 202 to permit 360 degree imaging of object 210.

Figure 23:
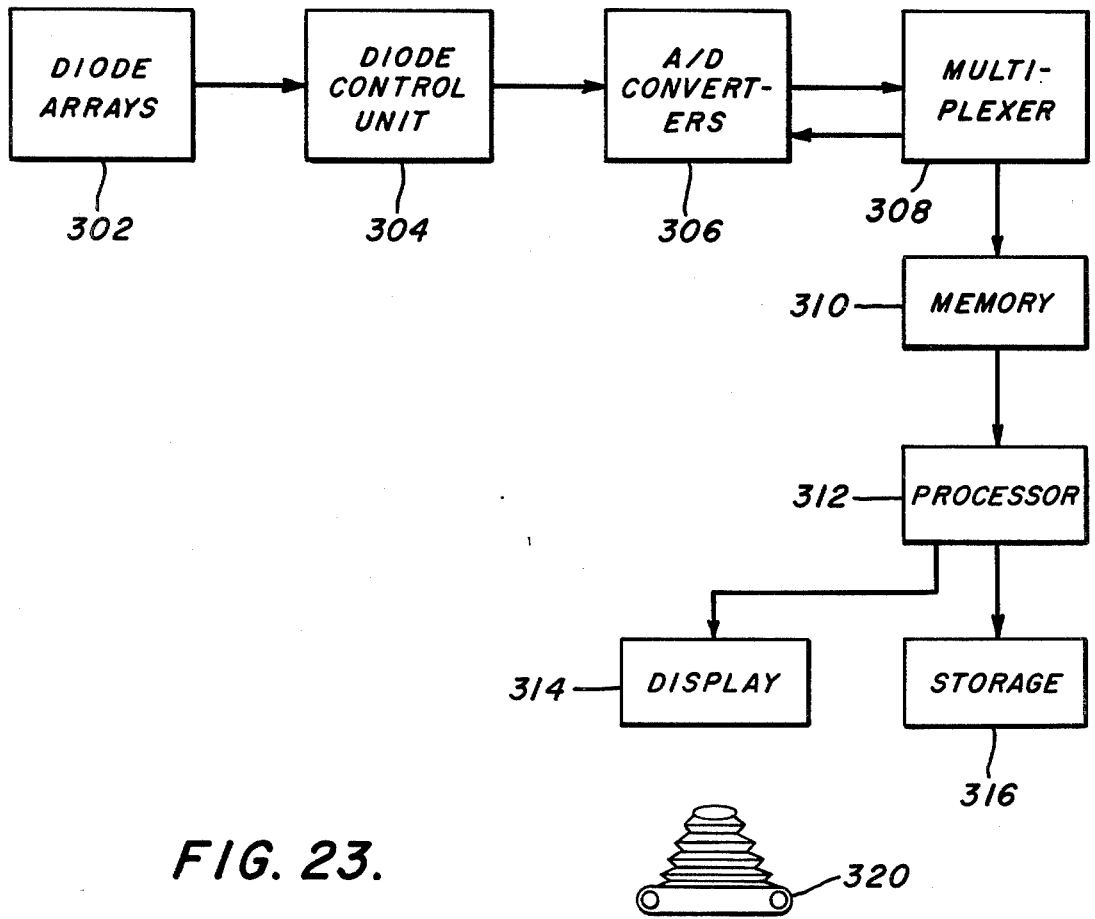
FIG. 23 illustrates a block diagram of a form of data processing means of the present invention.

Referring now to FIG. 23, a form of electrical processing means contemplated for use with the present invention will be discussed. As the components and sequence of operations are conventional and are well known to those skilled in the art, a detailed explanation is not deemed necessary at this point. The diode arrays 302 detect the optical images from the scintillator means by optical coupling means and convert the image into an electronic signal. The diodes are controlled by a diode control unit 304 and the signal goes to the analog to digital converter 306 which converts the analog signal to digital signals. The process is controlled by a multiplexer circuit 308 and the digital pulses go to the computer memory 310 for storage. The stored signals are digitally processed in the processor 312 and may be displayed on the display 314 and may also be stored for future use with the storage devices 316, such as magnetic discs or tapes, digital tape, storage tubes, digital computer memory, video tape, photographs or electron beam tape recorders. Also, camera 320 may be used to photograph the image on display 314.

It will, therefore, be appreciated that the present invention has provided apparatus for improving contrast sensitivity and detail of radiographic systems while permitting the use of reduced radiation exposure. In addition, the equipment is compatible with existing radiographic equipment, such as that presently used in diagnostic radiology and is inexpensive to manufacture and use. As a result of the compact size of the equipment, it may readily be used and stored without any inconvenience such as that frequently encountered with respect to some present conventional equipment. The system is adapted for use with a wide range of conventional and unconventional medical radiographic techniques involving pulsed or continuous x-rays, gamma rays and other forms of radiation, as well as other uses not found in the medical environment, such as in security systems and non-destructive testing, for example.

While the relationships in size between the scintillator means and the self-scanning photodiode array, be it linear or planar, such as rectangular, for example, frequently have been illustrated in the context of certain specific optical coupling means, it will be appreciated that other means may be employed, and most of the means described and illustrated in the present disclosure may be used interchangeably.

As the means for effecting simple mechanical movement of collimators and shutters, patient supporting tables, and support members, such as those used for scintillators, are well known and may be of any conventional variety and will be obvious to those skilled in the art, a detailed description of the same has not been provided herein.

While emphasis has been placed herein on the use of a scintillator which is physically separated from the selfscanning photodiode array by separate optical coupling means, it will be appreciated that, if desired, a scintillator material may be deposited, coated or laminated directly on the array with the interface therebetween serving as the optical coupling means, and such construction is expressly contemplated by this invention.

While for purposes of illustration collimators with a single slit have been emphasized herein, it will be appreciated that for certain uses more than one slit may be employed in a collimator.

While specific reference has been made to a radiation source providing x-rays or gamma rays, the invention is not so limited, and other forms of radiation, such as particulate radiation including protons and mesons, for example, may be employed. In connection with particulate radiation, as well as other forms, a generally rectangular beam having parallel sides may be used in lieu of a fan beam.

It will be apparent that various means may be employed to establish the relative movement desired for effecting radiation exposure. For example, in the embodiment of FIG. 1(a), the patient 14 may remain stationary, and the radiation source 2, scintillator means 22, lens 26 and array 30 moved.

While for purposes of simplicity of description herein, in general, the primary radiation beam has been illustrated as being either vertically or horizontally oriented, it will be appreciated that the present system is adapted for use with the primary radiation being at a wide range of angles including the full spectrum of ranges encountered in connection with computerized axial tomography.

Whereas, particular embodiments of the invention have been described above for purposes of illustration, it will be evident to those skilled in the art that numerous variations of the details may be made without departing from the invention as defined in the appended claims.

We claim:

1. Radiography apparatus comprising
   a source of radiation,
   collimator means interposed between said radiation source and an object to be exposed to radiation for converting said radiation into a generally fan-shaped beam,
   scintillator means disposed on the opposite side of said object from said radiation source for converting radiation into light,
   a self-scanning integrated array of photodiodes for receiving light produced by said radiation and emitting responsive electrical signals,
   optical coupling means connecting said scintillator means to said self-scanning photodiode array,
   said optical coupling means having fiber optic means operatively associated with said scintillator means and said self-scanning array of photodiodes, whereby light emitted by said scintillator means will be delivered with substantial continuity to said self-scanning array of photodiodes,
   signal receiving means operatively associated with said self-scanning photodiode array to store, process or display said image information,
   said self-scanning array of photodiodes being a planar array having at least two parallel rows of linear self-scanning photodiode arrays, and
   said self-scanning array of photodiodes having two said rows of linear self-scanning photodiode arrays, disposed with said linear arrays of a first said row being staggered with respect to said linear arrays of a second said row.

2. The radiography apparatus of claim 1 including said collimator means having at least one opening for controlling the amount of radiation impinging upon said object.

3. The radiography apparatus of claim 2 including means for establishing relative movement between said object and said collimator means, whereby portions of said object will be sequentially exposed to said radiation.

4. The radiography apparatus of claim 2 including said collimator means opening being so configurated as to permit a generally fan-shaped radiation beam to pass therethrough.

5. The radiography apparatus of claim 4 including said collimator means opening being a slit.

6. The radiography apparatus of claim 3 including movement establishing means having means for moving said collimator means while said radiation source, said object and said self-scanning array of photodiodes remain stationary.

7. The radiography apparatus of claim 3 including said movement establishing means having means for moving said radiation source and said collimator means while said object, said scintillator means, said optical coupling means and said self-scanning array of photodiodes remain stationary.

8. The radiography apparatus of claim 3 including said movement establishing means having means for moving said object while said radiation source, said collimator means, said scintillator means, said optical coupling means and said self-scanning array of photodiodes remain stationary.

9. The radiography apparatus of claim 3 including said movement establishing means having means for moving said radiation source, said scintillator means, said optical coupling means, said collimator means and said self-scanning array of photodiodes while said object remains stationary.

10. The radiography apparatus of claim 3 including said movement establishing means adapted to move said radiation source and said collimator means in an arc-shaped path about a center disposed generally at said scintillator means while said scintillator means, said optical coupling means and said self-scanning array of photodiodes remain stationary.

11. The radiography apparatus of claim 9 including said movement establishing means includes means for establishing orbital movement of said radiation source, said collimator means, said scintillator means, said optical coupling means and said self-scanning array of photodiodes about an axis passing through said object.

12. The radiography apparatus of claim 11 including said object being a patient and said axis passing longitudinally through said patient.

13. The radiography apparatus of claim 10 including object moving means for establishing movement of said object generally along the axis of said arc-shaped path.

14. The radiography apparatus of claim 13 including said object moving means having a table for supporting a human patient.

15. The radiography apparatus of claim 2 including said radiation source having an x-ray generator.

16. The radiography apparatus of claim 2 including said scintillator means having a fluorescent screen.

17. The radiography apparatus of claim 1 including said fiber optic means alternately connecting portions of said scintillator means with a photodiode array from said first row and a photodiode array from said second row, whereby adjacent portions of said scintillator means will be optically coupled to photodiode arrays in different rows.

18. The radiography apparatus for claim 17 including said photodiode arrays of one said row being so positioned with respect to said photodiode arrays of said other row that at least one transverse edge of an array of one said row will be substantially aligned with a transverse edge of an array of said other row, whereby appreciable gaps and overlaps will be substantially completely eliminated and substantially continuous image information will be created.

19. The radiography apparatus of claim 17 including a radiation opaque housing surrounding said scintillator means, optical coupling means and self-scanning photodiode arrays, and said housing having an opening generally aligned with said scintillator means.

20. The radiography apparatus of claim 1 including said fiber optic means being substantially coextensive with said scintillator means and said self-scanning array of photodiodes, and said fiber optic means having fibers of substantially uniform cross-sectional configuration throughout their length.

21. The radiography apparatus of claim 20 including the area of contact between said scintillator means and said fiber optic means being substantially equal to the area of contact between said fiber optic means and said self-scanning array of photodiodes.

22. The radiography apparatus of claim 2 including said self-scanning array of photodiodes includes a linear array of about 60 to 2048 photodiodes per linear inch.

23. The radiography apparatus of claim 22 including said self-scanning array of photodiodes includes more than one linear array of self-scanning photodiodes, and said arrays being oriented generally parallel with respect to each other.

24. The radiography apparatus of claim 2 including said fibers being tapered.

25. The radiography apparatus of claim 2 including said signal receiving means includes means to display an image corresponding to said electrical signals received from said self-scanning array of photodiodes.

26. The radiography apparatus of claim 2 including said signal receiving means includes means for storing image information.

27. The radiography apparatus of claim 2 including said signal receiving means includes digital computer means for modifying said electrical signals received from said self-scanning array of photodiodes to enhance portions of the image produced.

28. The radiography apparatus of claim 26 including said means for storing image information having means for storing said image information in digital form.

29. The radiography apparatus of claim 2 including second collimator means interposed between said object and said scintillator means.

30. The radiography apparatus of claim 29 including additional collimator means interposed between said optical coupling means and said self-scanning array of photodiodes.

31. The radiography apparatus of claim 2 including third collimator means interposed between said optical coupling means and said self-scanning array of photodiodes.

32. The radiography apparatus of claim 31 including said self-scanning array of photodiodes being a linear array.

33. The radiography apparatus of claim 1 including said self-scanning photodiode array having a plurality of parallel rows of linear self-scanning photodiode arrays.

34. Radiography apparatus comprising a source of radiation, collimator means interposed between said radiation source and an object to be exposed to radiation for converting said radiation into a generally fan-shaped beam, scintillator means disposed on the opposite side of said object from said radiation source for converting radiation into light, a self-scanning integrated array of photodiodes for receiving light produced by said radiation and emitting responsive electrical signals, optical coupling means connecting said scintillator means to said self-scanning photodiode array, signal receiving means operatively associated with said self-scanning photodiode array to store, process or display said image information, said collimator means having at least one opening for controlling the amount of radiation impinging upon said object, said radiation source having an x-ray generator, said collimator means including a hollow, generally cylindrical member, having at least one generally longitudinal slit and mounted for axial rotation or oscillation, said collimator means surrounding said x-ray source, a second generally cylindrical member having at least one generally longitudinal slit surrounding said self-scanning array of photodiodes and mounted for axial rotation or oscillation, and synchronizing means for coordinating rotation or oscillation of said cylindrical members, whereby a fan-shaped or rectangular x-ray beam emerging from a slot in said collimator cylindrical member will pass through and be partially absorbed by said object, will subsequently impinge upon said scintillator means which will emit responsive light which, in turn, will pass through a slit in second generally cylindrical means and impinge upon said self-scanning array of photodiodes.

35. Radiography apparatus comprising a source of radiation, collimator means interposed between said radiation source and an object to be exposed to radiation for converting said radiation into a generally fan-shaped beam, scintillator means disposed on the opposite side of said object from said radiation source for converting radiation into light, a self-scanning integrated array of photodiodes for receiving light produced by said radiation and emitting responsive electrical signals, optical coupling means connecting said scintillator means to said self-scanning photodiode array, signal receiving means operatively associated with said self-scanning photodiode array to store, process or display said image information, said self-scanning array of photodiodes being a planar array having at least two parallel rows of linear self-scanning photodiode arrays, electrical means for energizing portions of said planar array of self-scanning photodiodes, means for effecting movement of said collimator means, and said electrical means having means for energizing portions of said planar array in synchronized manner with respect to said collimator means movement.

36. Radiography apparatus comprising a source of radiation, scintillator means disposed on the exit side of an object for converting radiation to light, collimator means interposed between said object and said scintillator means, a self-scanning integrated array of photodiodes for receiving light produced by said radiation and emitting responsive electrical signals, optical coupling means connecting said scintillator means to said self-scanning photodiode array, said optical coupling means having fiber optic means operatively associated with said scintillator means and said self-scanning array of photodiodes, whereby light emitted by said scintillator means will be delivered with substantial continuity to said self-scanning array of photodiodes, signal receiving means operatively associated with said self-scanning photodiode array to store, process or display image information, said radiation source being a gamma ray emitting isotope disposed within said object, said collimator means being a Bucky type fine collimating grid, and said self-scanning array of photodiodes including two rows of staggered linear arrays.

* * * * *

UNITED STATES PATENT AND TRADEMARK OFFICE
CERTIFICATE OF CORRECTION

PATENT NO. : 4,179,100
DATED : December 18, 1979
INVENTOR(S) : Donald Sashin and Ernest J. Sternglass It is certified that error appears in the above-identified patent and that said Letters Patent are hereby corrected as shown below:

Page 1, left column under "U. S. PATENT DOCUMENTS", adjacent "3,833,810" change "5/1958" to "9/1974".

Page 1, left column under "U. S. DOCUMENTS", change "3,837,657" to "2,837,657".

Page 1, line 53, after "photomultipliers" change "of" to "or".

Column 4, line 51 after "object" change "13" to "14".

Signed and Sealed this

Fifteenth Day of July 1980

[SEAL]

Attest:

Attesting Officer

SIDNEY A. DIAMOND

Commissioner of Patents and Trademarks